US012715022B2

(12) United States Patent
Liu et al.

(10) Patent No.: US 12,715,022 B2
(45) Date of Patent: Aug. 25, 2026

(54) ULTRASOUND TRANSDUCER UNIT, ARRAY AND ULTRASONIC TREATMENT DEVICE

(71) Applicant: SHENZHEN PENINSULA MEDICAL GROUP, Shenzhen (CN)

(72) Inventors: Pengbo Liu, Shenzhen (CN); Yanan Li, Shenzhen (CN); Xiaobing Lei, Shenzhen (CN); Yujia Peng, Shenzhen (CN); Jianrong Luo, Shenzhen (CN); Zhibing Liu, Shenzhen (CN)

(73) Assignee: SHENZHEN PENINSULA MEDICAL GROUP, Shenzhen (CN)

( * ) Notice: Subject to any disclaimer, the term of this patent is extended or adjusted under 35 U.S.C. 154(b) by 0 days.

(21) Appl. No.: 19/021,132

(22) Filed: Jan. 14, 2025

(65) Prior Publication Data

US 2025/0303447 A1 Oct. 2, 2025

Related U.S. Application Data

(63) Continuation of application No. PCT/CN2024/114454, filed on Aug. 26, 2024.

(30) Foreign Application Priority Data

Mar. 29, 2024 (CN) ......................... 202410388613.0

(51) Int. Cl.
*B06B 1/06* (2006.01)
*A61N 7/00* (2006.01)

(52) U.S. Cl.
CPC .............. *B06B 1/0685* (2013.01); *A61N 7/00* (2013.01); *B06B 1/067* (2013.01); *A61N 2007/0078* (2013.01); *B06B 2201/76* (2013.01)

(58) Field of Classification Search
CPC ... B06B 1/0674; B06B 1/0677; B06B 1/0681; B06B 1/0685; A61N 7/00; A61N 2007/0078
See application file for complete search history.

(56) References Cited

U.S. PATENT DOCUMENTS

2007/0205697 A1 9/2007 Chaggares et al.
2009/0147627 A1* 6/2009 Toda ......................... B06B 1/06 156/60
2024/0017294 A1* 1/2024 Chaggares ............. H04R 17/10

FOREIGN PATENT DOCUMENTS

CN 101605288 A 12/2009
CN 105080822 A 11/2015
CN 112657817 A 4/2021
CN 117018479 A * 11/2023 ............... A61N 7/00

OTHER PUBLICATIONS

International Search Report and Written Opinion issued in corresponding PCT Application No. PCT/CN2024/114454, dated Nov. 23, 2024.

* cited by examiner

*Primary Examiner* — Chao Sheng
(74) *Attorney, Agent, or Firm* — Westbridge IP LLC

(57) ABSTRACT

Disclosed are an ultrasonic transducer unit, an array and an ultrasonic treatment device. The ultrasonic transducer unit includes a backing layer, a heavy backing layer, a piezoelectric layer and a matching layer stacked in sequence. The thickness of the piezoelectric layer ranges from 0.125 times of the wavelength to 0.25 times of the wavelength, excluding 0.25 times of the wavelength. The wavelength refers to the wavelength of the wave at the center frequency of the ultrasonic transducer unit in the piezoelectric layer.

12 Claims, 5 Drawing Sheets

Time (μs)

Time (μs)

ULTRASOUND TRANSDUCER UNIT, ARRAY AND ULTRASONIC TREATMENT DEVICE

CROSS-REFERENCE TO RELATED APPLICATIONS

The present application is a continuation application of International Application No. PCT/CN2024/114454, filed on Aug. 26, 2024, which claims priority to Chinese Patent Application No. 202410388613.0, filed on Mar. 29, 2024. The entire contents of the above-mentioned applications are incorporated herein by reference.

TECHNICAL FIELD

The present application relates to the technical field of ultrasonic transducers, and in particular to an ultrasonic transducer unit, an array and an ultrasonic treatment device.

BACKGROUND

The ultrasonic transducer unit is an important component of ultrasonic testing equipment, which can convert electromagnetic energy into mechanical energy (sound energy). The piezoelectric layer, matching layer and backing layer are the core components of the ultrasonic transducer unit. The thickness of the piezoelectric layer in the current ultrasonic transducer unit can be a quarter wavelength ($\lambda/4$), and a heavy backing layer is provided between the piezoelectric layer and the backing layer.

Compared to a piezoelectric layer with a thickness of one-half wavelength ($\lambda/2$), a piezoelectric layer with a thickness of one-quarter wavelength is thinner and can avoid acoustic interference from behind the piezoelectric layer through the heavy backing layer, improving the bandwidth of the transducer. However, the thickness of the piezoelectric layer is still relatively thick, and the area of the piezoelectric layer is also relatively large, which results in a relatively large volume of the ultrasonic transducer unit, making it difficult to achieve miniaturization.

However, the selection of $\lambda/4$ as the thickness of the piezoelectric layer is only a theoretical value. In practical applications, when the piezoelectric layer vibrates to generate ultrasonic energy under the high-frequency voltage signals applied to its upper and lower electrodes, it is affected by other layers above and below it, resulting in an actual output of ultrasonic energy that is lower than the ideal maximum output. It is usually necessary to increase the number (volume) of array elements of the transducer unit. This increases the volume, reduces the energy conversion efficiency, and increases heat generation, resulting in a further increase in the heat dissipation volume.

Therefore, how to solve the above technical problems should be the focus of those skilled in the art.

SUMMARY

The purpose of the present application is to provide an ultrasonic transducer unit, an array and an ultrasonic treatment device to reduce the volume of the ultrasonic transducer unit and enhance support performance of a piezoelectric layer.

In order to solve the above technical problems, the present application provides an ultrasonic transducer unit, including a backing layer, a heavy backing layer, a piezoelectric layer; and a matching layer stacked in sequence;

a thickness of the piezoelectric layer ranges from 0.125 times of a wavelength to 0.25 times of the wavelength, excluding 0.25 times of the wavelength;

a contact surface between the heavy backing layer and the piezoelectric layer is defined as a nodal plane of vibration, and when the piezoelectric layer vibrates, a displacement of the contact surface in a vibration direction is zero;

the wavelength refers to a wavelength of a wave at a center frequency of the ultrasonic transducer unit in the piezoelectric layer.

In an embodiment, a thickness of the heavy backing layer ranges from five times of the wavelength to ten times of the wavelength.

In an embodiment, a thickness of the heavy backing layer ranges from 0.25 times of the wavelength to 1.25 times of the wavelength.

In an embodiment, the heavy backing layer has an acoustic impedance greater than an acoustic impedance of the piezoelectric layer.

In an embodiment, the acoustic impedance of the heavy backing layer is 3 to 5 times of the acoustic impedance of the piezoelectric layer.

In an embodiment, the heavy backing layer comprises tungsten or a tungsten alloy.

In an embodiment, the ultrasonic transducer unit further includes a conductive layer provided between the piezoelectric layer and the heavy backing layer.

In an embodiment, at least two matching layers are provided, and the matching layer in direct contact with the piezoelectric layer has an acoustic impedance greater than an acoustic impedance of the piezoelectric layer.

In an embodiment, a surface of the backing layer away from the heavy backing layer is an arc surface with a Gaussian curvature greater than zero.

The present application also provides an ultrasonic transducer array, including two or more ultrasonic transducer units as described above.

In an embodiment, a gap is provided between adjacent ultrasonic transducer units, and the gap is filled with an insulating medium; the gap is distributed between a heavy backing layer and a matching layer, and the ultrasonic transducer unit further includes a conductive channel penetrating the heavy backing layer.

The present application also provides an ultrasonic treatment device, including the ultrasonic transducer unit or the ultrasonic transducer array as described above.

The ultrasonic transducer unit provided by the present application includes a backing layer, a heavy backing layer, a piezoelectric layer and a matching layer stacked in sequence. The thickness of the piezoelectric layer ranges from 0.125 times of the wavelength to 0.25 times of the wavelength, excluding 0.25 times of the wavelength. The wavelength refers to the wavelength of the wave with the center frequency of the ultrasonic transducer unit in the piezoelectric layer.

Therefore, the ultrasonic transducer unit of the present application includes a backing layer, a heavy backing layer, a piezoelectric layer and a matching layer. The thickness of the piezoelectric layer is relatively thin, less than 0.25 times of the wavelength, and is 0.125 times of the wavelength to 0.25 times of the wavelength. According to the relationship between the thickness and area of the piezoelectric layer, the area of the piezoelectric layer will have a larger reduction space, so that a smaller ultrasonic transducer can be made to achieve product miniaturization. Since the thickness and area of the piezoelectric layer are reduced, the volume of the ultrasonic transducer unit becomes smaller, making the ultrasonic transducer unit have the characteristics of miniaturization. In addition, further thinning the piezoelectric layer can offset the influence of the acoustic impedance of the heavy backing layer on the composite impedance of the device, so that the actual energy output of the ultrasonic transducer unit is higher.

In addition, the present application also provides an ultrasonic transducer array and an ultrasonic treatment device having the above advantages.

BRIEF DESCRIPTION OF THE DRAWINGS

In order to more clearly explain technical solutions in the embodiments of the present application or in the related art, accompanying drawings required in the description of the embodiments or the related art will be briefly introduced below. Obviously, the accompanying drawings in the following description are only some embodiments of the present application. For those skilled in the art, other drawings can be obtained based on the structures shown in these drawings without creative efforts.

DETAILED DESCRIPTION OF THE EMBODIMENTS

In order to enable those skilled in the art to better understand the solution of the present application, the present application will be further described in detail below in conjunction with the accompanying drawings and specific embodiments. Obviously, the described embodiments are only some rather than all of the embodiments of the present application. Based on the embodiments in the present application, all other embodiments obtained by those skilled in the art without creative efforts fall within the scope of the present application.

Many specific details are set forth in the following description to fully understand the present application. However, the present application can also be implemented in other ways different from those described here. Modifications can be made by those skilled in the art without departing from the scope of the present application. Accordingly, the present application is not limited to the specific embodiments described below.

As described in the background, the piezoelectric layer of the ultrasonic transducer unit in the related art has a thickness of one-quarter wavelength, which is still relatively thick. Moreover, according to the relationship between the thickness and area of the piezoelectric layer, the area of the piezoelectric layer is also relatively large, which leads to a relatively large volume of the ultrasonic transducer unit, making miniaturization difficult.

Figure 1:
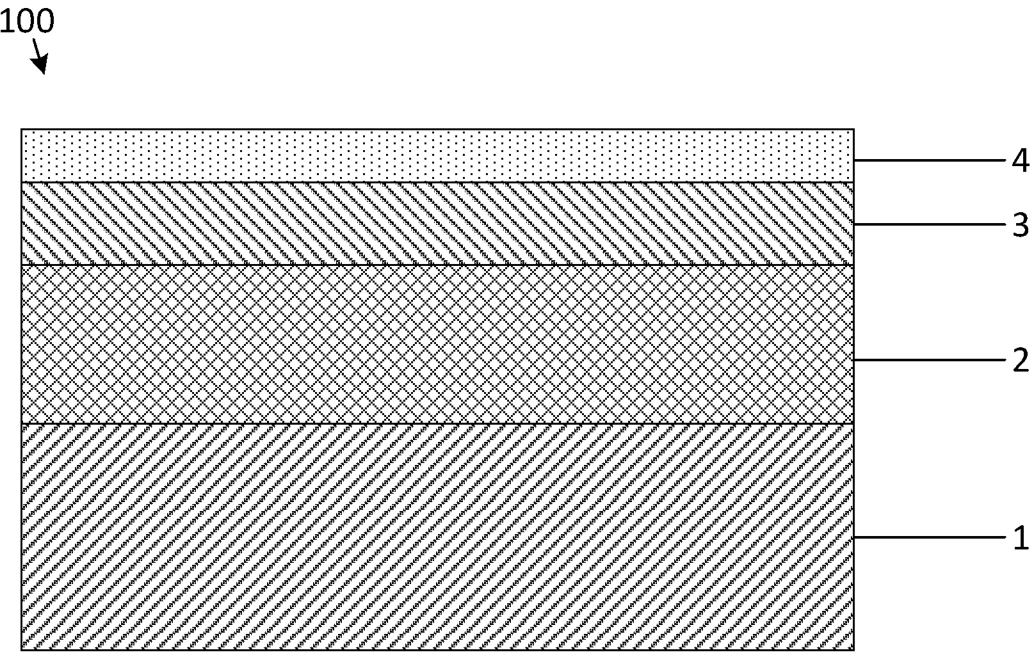
FIG. 1 is a schematic structural view of an ultrasonic transducer unit according to an embodiment of the present application.

In view of this, the present application provides an ultrasonic transducer unit, as shown in FIG. 1, including a backing layer 1, a heavy backing layer 2, a piezoelectric layer 3 and a matching layer 4 are stacked in sequence. The thickness of the piezoelectric layer 3 ranges from 0.125 times of the wavelength to 0.25 times of the wavelength, excluding 0.25 times of the wavelength.

The wavelength (λ) in the present application always refers to the wavelength of the wave at a central frequency of the ultrasonic transducer unit in the piezoelectric layer.

The ultrasonic transducer unit 100 in this embodiment may be a non-focused ultrasonic transducer or a focused ultrasonic transducer.

When a voltage is applied to the piezoelectric layer 3, the piezoelectric layer 3 converts electrical energy into mechanical energy of ultrasonic waves to generate ultrasonic waves. The ultrasonic wave generated by the piezoelectric layer 3 propagates both forward (a direction from the piezoelectric layer 3 to the matching layer 4) and backward (a direction from the piezoelectric layer 3 to the backing layer 1).

The backing layer 1 is configured to absorb the vibration energy that may be transmitted from the piezoelectric layer 3 to the backing layer 1, and serves as a structural support and a heat dissipation layer.

The materials of the piezoelectric layer 3 include, but are not limited to, ceramics, single crystals, and polymers, such as lead zirconate titanate ceramics, single crystals formed of lead niobium zirconate titanate, and the like.

The thickness of the piezoelectric layer 3 ranges from 0.125 times of the wavelength (λ/8) to 0.25 times of the wavelength (λ/4). For example, the thickness of the piezoelectric layer 3 can be λ/8, λ/7, λ/6, λ/5, etc., and can be set as needed, but must be less than ¼ the wavelength. In an embodiment, the thickness of the piezoelectric layer 3 is between 0.125λ and 0.225λ.

Specifically, due to the existence of the heavy backing layer 2, the vibration of the back surface of the piezoelectric layer 2 is blocked. With its higher acoustic impedance and high sound speed characteristics, the "comprehensive vibration wavelength" of the entire unit device changes. Therefore, the thickness of the piezoelectric layer 2 needs to be less than 0.25λ to achieve the maximum amplitude and output the maximum energy. In the related art, the technical solution of λ/4 is directly adopted, ignoring the influence of other layers on the vibration characteristics of the piezoelectric layer, and actually cannot achieve the maximum energy output.

In order to ensure that the vibration mainly vibrates in the direction perpendicular to the piezoelectric layer 3 and reduces vibration in other directions, the area of the piezoelectric layer 3 is many times greater than the thickness of the piezoelectric layer 3. If the thickness of the piezoelectric layer 3 increases, an increment of the lower limit of the area of the piezoelectric layer 3 will be relatively large. Compared with the related art, since the thickness of the piezoelectric layer 3 in the present application is thinner, the area of the piezoelectric layer 3 in the present application can also be reduced, thereby reducing the overall volume of the ultrasonic transducer unit 100, facilitating miniaturization and microminiaturization.

The acoustic impedance of the matching layer 4 matches the acoustic impedance of the piezoelectric layer 3 to maximize the transmission of the ultrasonic waves generated by the piezoelectric layer 3 and reduce the loss of ultrasonic waves.

Figure 2:
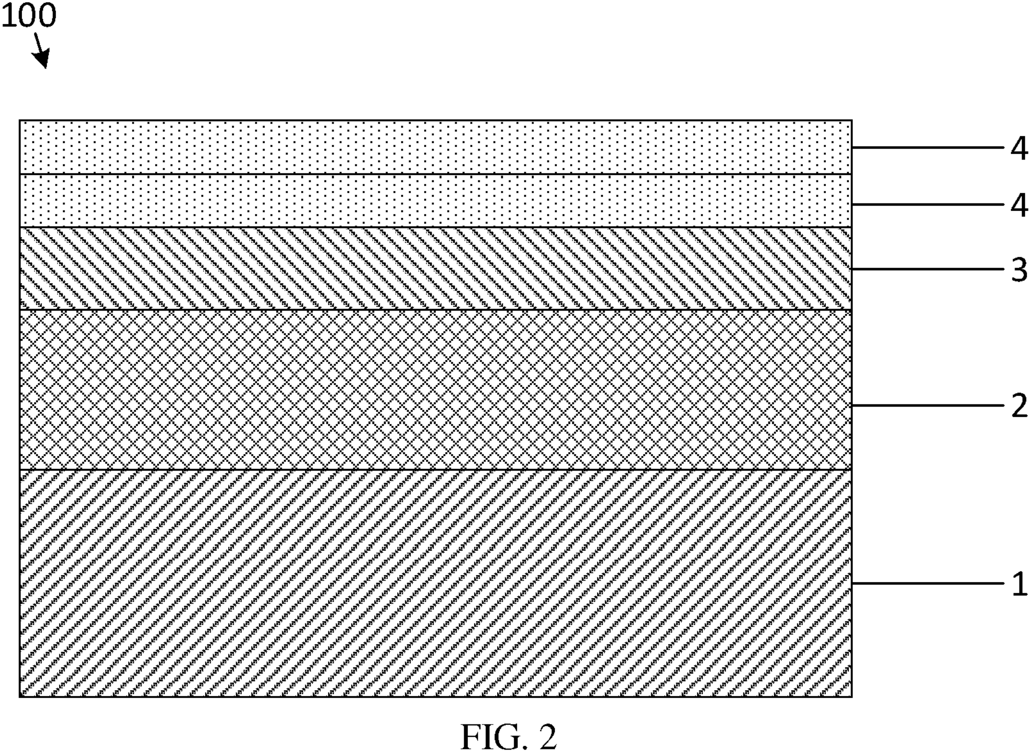
FIG. 2 is a schematic structural view of an ultrasonic transducer unit according to an embodiment of the present application.

In an embodiment, the matching layer 4 may be one layer, which is not limited in the present application. In another embodiment, the matching layer 4 may be at least two layers. When the matching layer 4 is two layers, as shown in FIG. 2.

When the matching layers 4 has at least two layers, the acoustic impedance of the matching layer 4 in direct contact with the piezoelectric layer 3 is greater than that of the piezoelectric layer 3 to improve the penetration of the sound beam.

The heavy backing layer 2 serves to block the backward vibration of the piezoelectric layer 3 to change the double-sided vibration of the piezoelectric layer 3 into single-sided vibration. A contact surface of the heavy backing layer 2 and the piezoelectric layer 3 is defined as a nodal plane of vibration. When the piezoelectric layer 3 vibrates, the displacement of the contact surface in the vibration direction is zero (or nearly zero). This concentrates the vibration of the piezoelectric layer 3 on the surface facing the emission direction.

In an embodiment, the acoustic impedance of the heavy backing layer 2 is greater than the acoustic impedance of the piezoelectric layer 3 to improve the ability of the heavy backing layer 2 to reflect ultrasonic waves.

In order to further improve the reflection of backward propagating ultrasonic waves, so that the ultrasonic energy can be transmitted forward, thereby generating a stronger signal sensitivity, while reducing the vibration on the back side, the acoustics impedance difference between the heavy backing layer 2 and the piezoelectric layer 3 can be increased. In an embodiment, the acoustic impedance of the heavy backing layer 2 is 3 to 5 times of the acoustic impedance of the piezoelectric layer 3. For example, the acoustic impedance of the heavy backing layer 2 is 3 times, 4 times, 5 times, etc., of the acoustic impedance of the piezoelectric layer 3, depending on the situation.

In case of different thicknesses of the heavy backing layer 2, the emission response of the ultrasonic transducer unit has different characteristics in terms of output energy and different dimensions of the waveform. The simulation results are shown in Table 1.

In an embodiment, the thickness of the heavy backing layer 2 ranges from 0.25 times of the wavelength to 1.25 times of the wavelength, which can keep the emission response at a high level. For example, the thickness of the heavy backing layer 2 may be 0.25λ, 0.3λ, 0.5λ, 0.8λ, λ, 1.25λ, etc. When the thickness of the heavy backing layer 2 is less than 0.25λ, the ultrasonic wave will penetrate the heavy backing layer (the simulation data in Table 1 cannot be shown, and the simulation model used cannot identify the ultrasonic penetration). This results in a large amount of energy propagating backward instead of forward, generating a large amount of heat. When the thickness of the heavy backing layer 2 is greater than 1.25λ, it leads to serious energy attenuation and reduces the ultrasonic emission energy. Therefore, for an ultrasonic treatment device for the purpose of thermal effect treatment, the ultrasonic transducer unit of the present application preferably has the heavy backing layer with a thickness of 0.25λ-1.25λ. Although the ultrasonic transducer with a thick heavy backing layer produces an output waveform containing more noise, it has a higher total output energy. If the piezoelectric layer has a thickness of 0.125λ-0.25λ, of which 0.25λ is excluded, it can have better treatment efficiency.

The heavy backing layer 2 has high strength, providing excellent mechanical support for the piezoelectric layer 3. Moreover, the heavy backing layer 2 avoids being driven by the piezoelectric layer 3 to vibrate, ensuring good acoustic reflection for the piezoelectric layer 3. Consequently, it can effectively reduce the heat generated by the backing layer 1 absorbing the sound waves propagating to it, ensuring the normal operation of the piezoelectric layer 3, and simultaneously enhancing the energy output of the transducer.

TABLE 1

| Thickness of heavy backing layer | Ultrasonic transducer unit emission response (KPa) |
|---|---|
| 0.20 λ | 2.99 |
| 0.25 λ | 3.27 |
| 0.30 λ | 3.14 |
| 0.50 λ | 2.62 |
| 1.00 λ | 2.35 |
| 1.25 λ | 2.22 |
| 1.50 λ | 2.15 |
| 1.75 λ | 2.17 |
| 2.00 λ | 2.15 |
| 2.50 λ | 2.12 |
| 3.00 λ | 2.11 |

In the embodiment of the present application, when the ultrasonic transducer is applied to the subdivided technical field of detection, in order to improve the detection sensitivity and reduce stray waves, the thickness of the heavy backing layer is preferably 5λ-10λ. As shown in FIG. 6A to FIG. 6D, which are simulated data diagrams of the output waveform of the ultrasonic transducer unit in case of different thicknesses of the heavy backing layer. The horizontal axis is time and the vertical axis is amplitude. When the thickness of the heavy backing layer 2 is less than 5λ (for example, 2.5λ), the waveform exhibits multiple sets of beams, and when the thickness of the heavy backing layer 2 is 5λ, the waveform exhibits a single set of beams. In the field of detection applications, a single set of beams has less noise, is easier to identify, and has high sensitivity. When the thickness of the heavy backing layer 2 exceeds 10λ (for example, 20λ), the waveform does not change significantly, but the pulse width narrows, which is not conducive to measurement. In addition, excessive thickness results in a significantly large vibration impedance, leading to insufficient overall energy output.

It should be noted that the material of the heavy backing layer 2 is not limited in this embodiment. In an embodiment, the heavy backing layer 2 is made of tungsten or tungsten alloy (such as carbon-tungsten alloy) and other metal materials with good electrical conductivity, to enhance the electrical conductivity of the heavy backing layer 2, thereby facilitating the transfer of charges generated by the vibration of the piezoelectric layer 3 to the acoustic impedance interface.

The ultrasonic transducer unit 100 of this embodiment includes a backing layer 1, a heavy backing layer 2, a piezoelectric layer 3 and a matching layer 4. The thickness of the piezoelectric layer 3 is relatively thin, ranging from 0.125 times of the wavelength to 0.25 times of the wavelength (0.25 times of the wavelength is excluded). According to the relationship between the thickness and area of the piezoelectric layer, the area of the piezoelectric layer 3 also gets decreased. Since the thickness and area of the piezoelectric layer are decreased, the volume of the ultrasonic transducer unit 100 becomes smaller, so that the ultrasonic transducer unit 100 has the characteristics of miniaturization.

Figure 3:
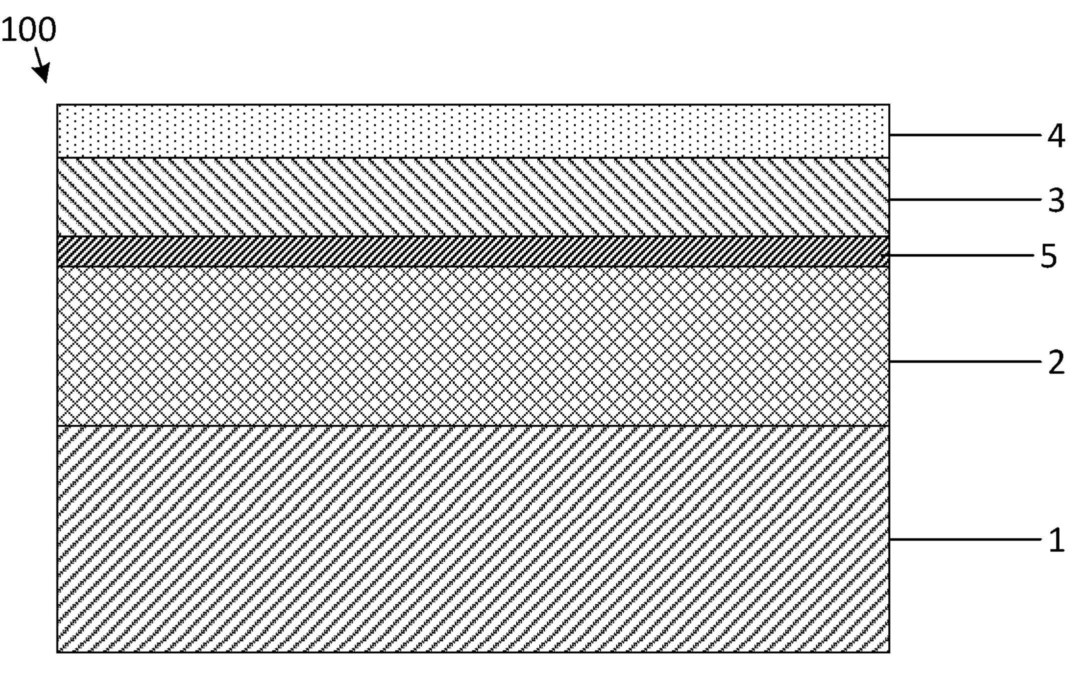
FIG. 3 is a schematic structural view of an ultrasonic transducer unit according to an embodiment of the present application.

Based on the above embodiments, in an embodiment of the present application, as shown in FIG. 3, the ultrasonic transducer unit 100 further includes a conductive layer 5.

The conductive layer 5 is provided between the piezoelectric layer 3 and the heavy backing layer 2.

The conductive layer 5 includes at least one of copper foil, gold foil and silver foil, etc.

The conductive layer 5 serves as an electrode of the piezoelectric layer 3 (the other electrode is provided between the piezoelectric layer 3 and the matching layer 4), and is electrically connected to a circuit (not shown) to control the potential difference between the two opposite surfaces of the piezoelectric layer 3.

In the structure composed of piezoelectric layer 3—conductive layer 5—heavy backing layer 2—circuit, the heavy backing layer 2 can be used as a part of the circuit, or can be just a non-electrical support structure.

It is understood that when the heavy backing layer 2 has sufficiently strong electrical conductivity, for example, when the material of the heavy backing layer 2 is tungsten or a tungsten alloy, the conductive layer 5 is not needed, in this case, eliminating the conductive layer lowers production complexity and cost, furthermore, reduces additional acoustic wave reflection, especially in high-frequency ultrasonic transducers.

Figure 4:
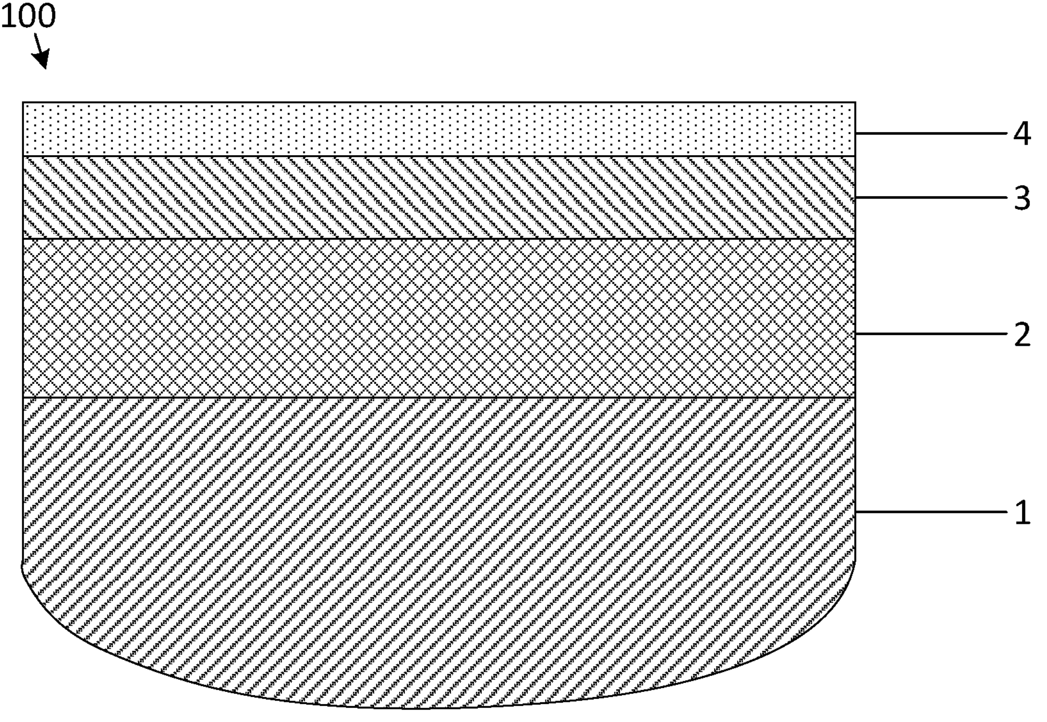
FIG. 4 is a schematic structural view of an ultrasonic transducer unit according to an embodiment of the present application.

Based on any of the above embodiments, in an embodiment of the present application, as shown in FIG. 4, the surface of the backing layer 1 away from the heavy backing layer 2 is an arc surface with a Gaussian curvature greater than zero.

On the one hand, the arc surface of the backing layer 1 can reflect the sound energy that has not been fully absorbed and change its propagation path. On the other hand, when the ultrasonic transducer unit 100 is packaged inside the shell, the surface connected to the shell is the arc surface, which can reduce the space occupied, thereby reducing the size of the shell.

In a specific embodiment, the backing layer 1 includes a first columnar part and a second arc-conical part away from the piezoelectric layer 3. The second arc-conical part includes an arc surface with a Gaussian curvature greater than zero. The second arc-conical part can change the transmission direction of the sound wave to prevent the sound wave from returning to and/or converging on the piezoelectric layer. The first columnar part can dissipate energy during transmission process of the sound wave and weaken possible reflected echo.

The present application also provides an ultrasonic transducer array, which includes two or more ultrasonic transducer units 100 described in any of the above embodiments.

The ultrasonic transducer array can be a linear multi-unit ultrasonic transducer array, that is, two or more ultrasonic transducer units 100 are arranged in a row; or the ultrasonic transducer array can be a two-dimensional area array ultrasonic transducer array, that is, two or more ultrasonic transducer units 100 are arranged in the form of m rows and n columns, of which m and n are integers greater than or equal to 2, m and n may be equal or unequal.

Figure 5:
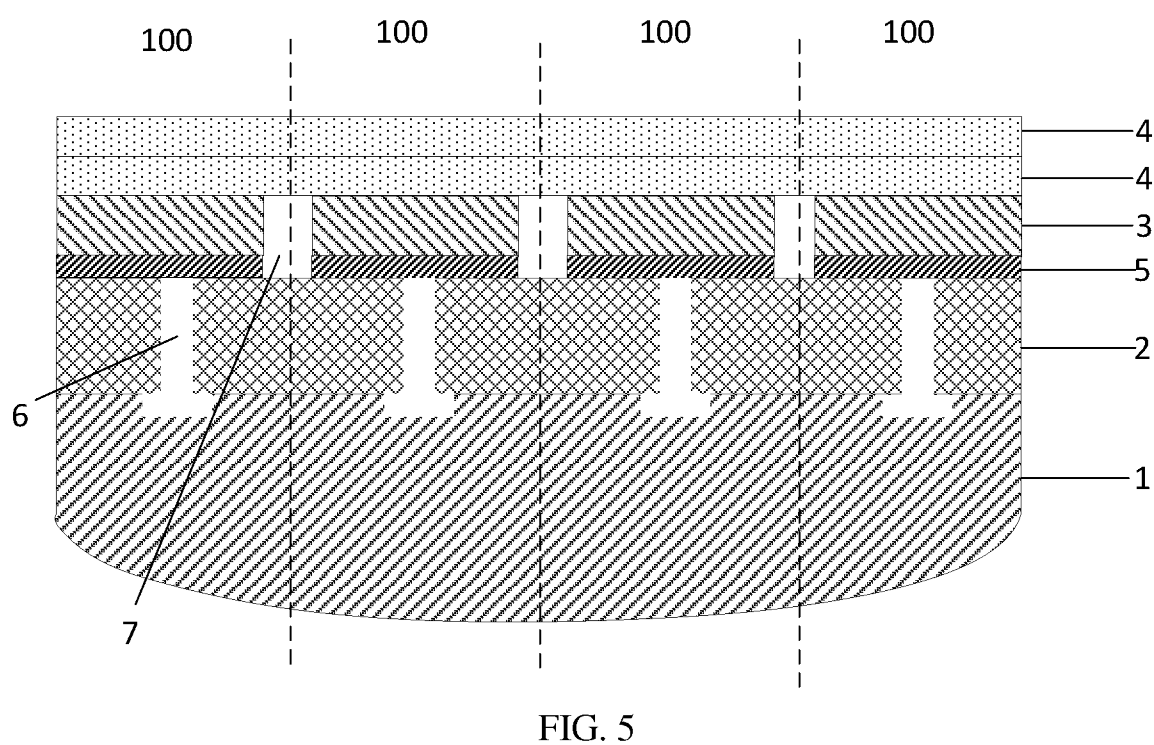
FIG. 5 is a schematic structural view of an ultrasonic transducer array according to an embodiment of the present application.
Figure 6A:
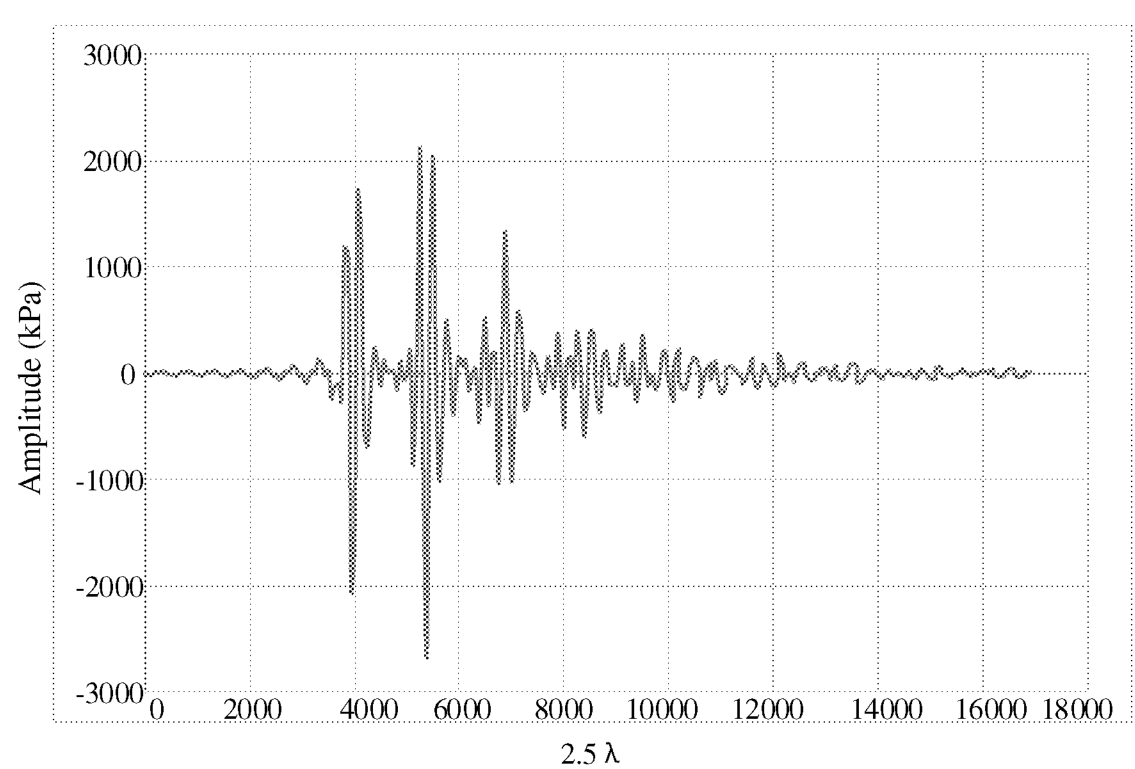
FIG. 6A is a simulation data diagram of an output waveform of the ultrasonic transducer unit in case of different thicknesses of a heavy backing layer.
Figure 6B:
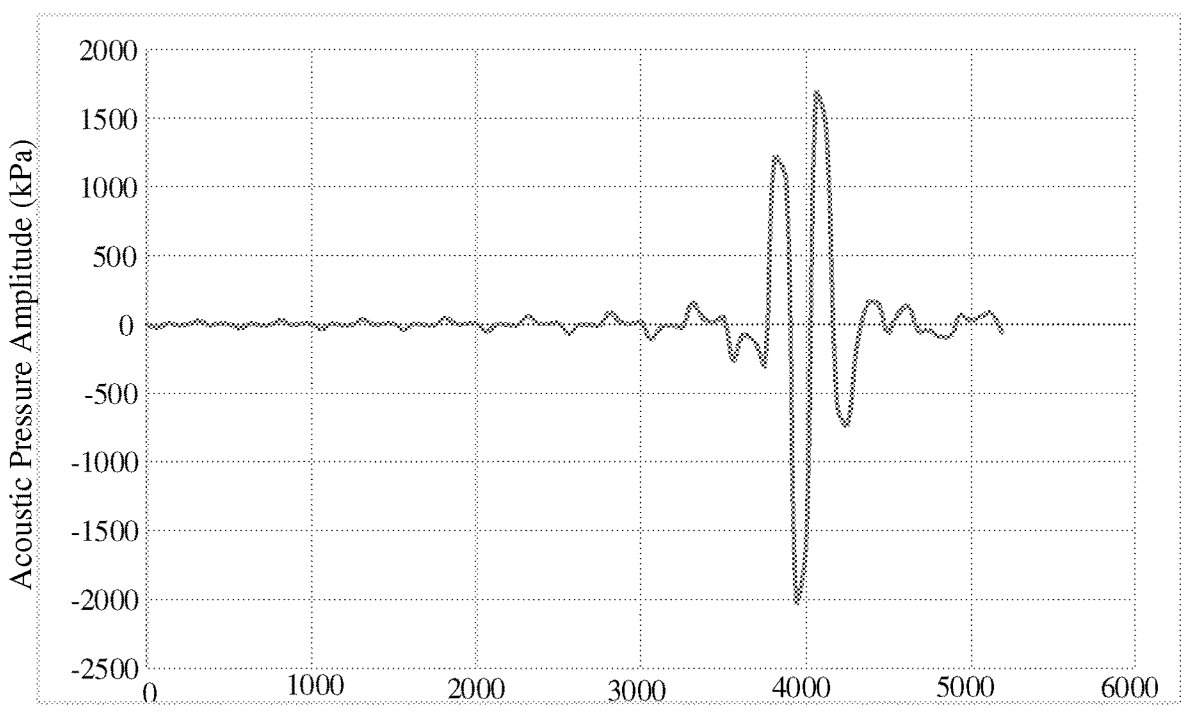
FIG. 6B is a simulation data diagram of an output waveform of the ultrasonic transducer unit in case of different thicknesses of a heavy backing layer.
Figure 6B:
Figure 6C:
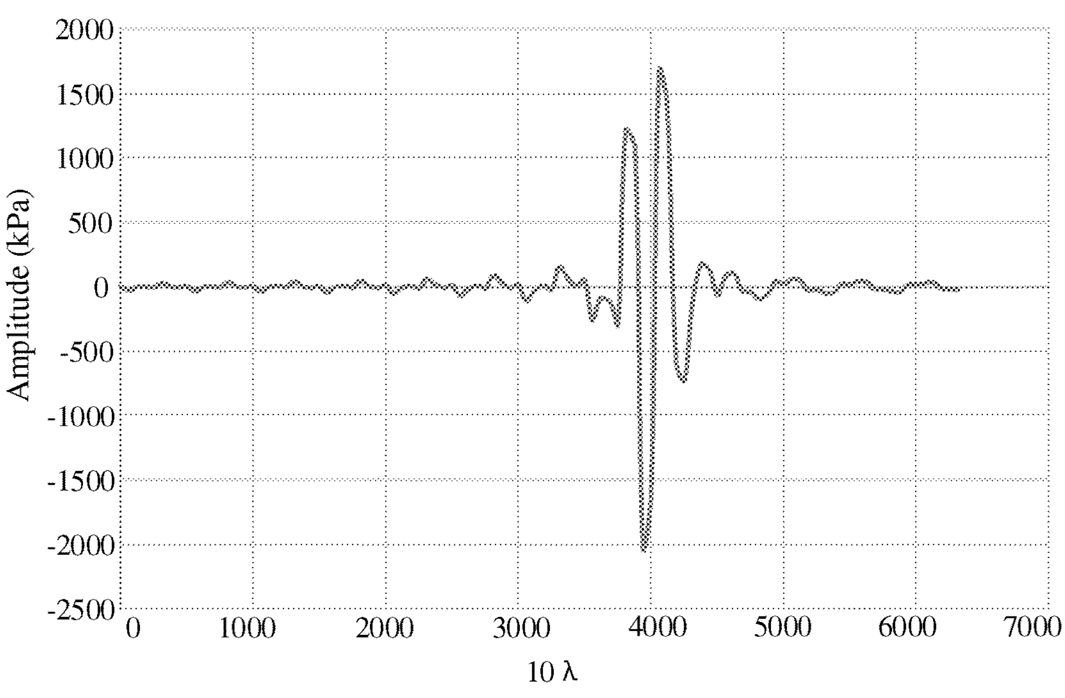
FIG. 6C is a simulation data diagram of an output waveform of the ultrasonic transducer unit in case of different thicknesses of a heavy backing layer.
Figure 6D:
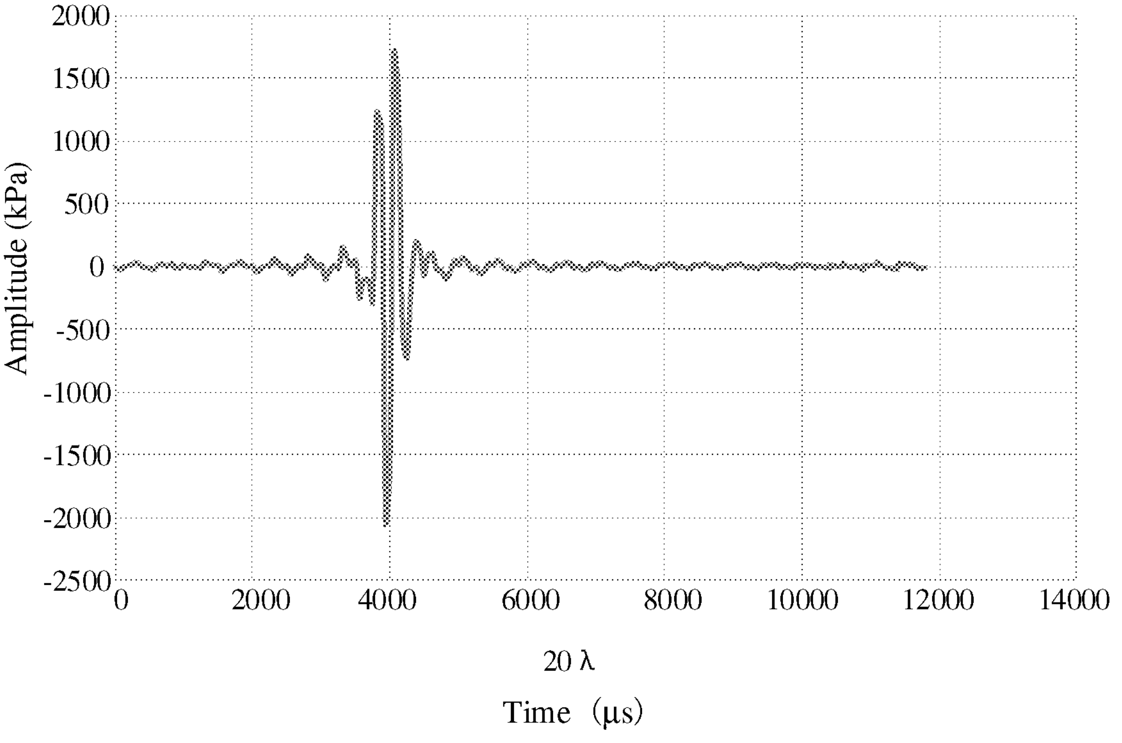
FIG. 6D is a simulation data diagram of an output waveform of the ultrasonic transducer unit in case of different thicknesses of a heavy backing layer.

As shown in FIG. 5, a gap 7 is provided between adjacent ultrasonic transducer units 100. The gap 7 is filled with an insulating medium. The gap 7 is distributed between the heavy backing layer 2 and the matching layer 4.

The insulating medium includes insulating materials, such as epoxy resin.

Filling the insulating medium in the gap 7, on the one hand, can enhance the strength of the ultrasonic transducer array and avoid breakage in the gap 7; on the other hand, it can also prevent short circuits.

The gap 7 does not extend into the matching layer 4 and the heavy backing layer 2, in other words, the matching layers 4 of all of the ultrasonic transducer units 100 in the ultrasonic transducer array are connected together, resulting in better support. When the ultrasonic transducer unit 100 includes the conductive layer 5, the gap 7 extends to the conductive layer 5.

The ultrasonic transducer unit 100 also includes a conductive channel 6 penetrating the heavy backing layer 2. The conductive channel 6 is filled with a conductive medium and can connect the conductive layer 5 with an external control circuit to control the piezoelectric layer 3. In this embodiment, the heavy backing layer 2 does not act as a conductive layer to avoid short circuits.

The present application also provides an ultrasonic treatment device for treating skin tissue by transmitting thereto ultrasonic vibrations generated by means of an ultrasonic transducer unit or an ultrasonic transducer array, which includes the ultrasonic transducer unit 100 or the ultrasonic transducer array described in any of the above embodiments.

A specific example is provided below to illustrate the preparing method for the ultrasonic transducer unit 100 in any of the above embodiments.

Step 1, bonding two matching layers on the matching surface of the piezoelectric layer; in which the piezoelectric layer may be a piezoelectric ceramic chip.

Step 2, bonding, using glue, a conductive layer on the other side of the piezoelectric layer, in which the conductive layer may be copper foil.

Step 3, bonding the heavy backing layer on the surface of the conductive layer.

Step 4, drilling holes into the conductive layer on the surface of the heavy backing layer away from the conductive layer, but the holes do not penetrate the conductive layer; in which the drilling may use laser cutting, wet etching or ion beam etching.

Step 5, bonding the conductive electrodes inside the drilled holes.

Step 6, bonding the backing layer on the surface of the heavy backing layer.

Each embodiment in this description is described in a progressive manner. Each embodiment focuses on its differences from other embodiments. The same or similar parts between the various embodiments can be referred to each other.

The ultrasonic transducer unit and array, and the ultrasonic treatment device provided by the present application have been described in detail above. The specific embodiments have been used in this article to illustrate the principles and implementation methods of the present application. The description of the above embodiments is only used to help understand the solution and the core idea of the present application. It should be noted that for those skilled in the art, some improvements and modifications can be made to the present application without departing from the principles of the present application, and these improvements and modifications also fall within the scope of the present application.

What is claimed is:

1. An ultrasonic transducer unit, comprising a backing layer;

a heavy backing layer;

a piezoelectric layer; and a matching layer, wherein the backing layer, the heavy backing layer, the piezoelectric layer and the matching layer are stacked in sequence;

a thickness of the piezoelectric layer ranges from 0.125 times of a wavelength to 0.25 times of the wavelength, excluding 0.25 times of the wavelength;

the heavy backing layer is configured to damp vibration of a back surface of the piezoelectric layer to substantially zero vibration;

a contact surface between the heavy backing layer and the piezoelectric layer is defined as a nodal plane of vibration; and when the piezoelectric layer vibrates, a displacement of the contact surface in a vibration direction is zero, and the wavelength refers to a wavelength of a wave at a center frequency of the ultrasonic transducer unit in the piezoelectric layer.

2. The ultrasonic transducer unit of claim 1, wherein a thickness of the heavy backing layer ranges from five times of the wavelength to ten times of the wavelength.

3. The ultrasonic transducer unit of claim 1, wherein a thickness of the heavy backing layer ranges from 0.25 times of the wavelength to 1.25 times of the wavelength.

4. The ultrasonic transducer unit of claim 1, wherein the heavy backing layer comprises tungsten or a tungsten alloy.

5. The ultrasonic transducer unit of claim 1, further comprising a conductive layer provided between the piezoelectric layer and the heavy backing layer.

6. The ultrasonic transducer unit of claim 1, further comprising at least two matching layers, wherein the matching layer in direct contact with the piezoelectric layer has an acoustic impedance greater than an acoustic impedance of the piezoelectric layer.

7. The ultrasonic transducer unit of claim 1, wherein a surface of the backing layer away from the heavy backing layer is an arc surface with a Gaussian curvature greater than zero.

8. An ultrasonic treatment device, comprising an ultrasonic transducer array comprising two or more ultrasonic transducer units of claim 1.

9. The ultrasonic transducer unit of claim 1, wherein the heavy backing layer has an acoustic impedance greater than an acoustic impedance of the piezoelectric layer.

10. The ultrasonic transducer unit of claim 9, wherein the acoustic impedance of the heavy backing layer is 3 to 5 times of the acoustic impedance of the piezoelectric layer.

11. An ultrasonic transducer array, comprising two or more ultrasonic transducer units of claim 1.

12. The ultrasonic transducer array of claim 11, wherein a gap is provided between adjacent ultrasonic transducer units, and the gap is filled with an insulating medium; the gap is distributed between a heavy backing layer and a matching layer, and the ultrasonic transducer unit further comprises a conductive channel penetrating the heavy backing layer.

* * * * *